United States Patent [19]
Lee et al.

[11] Patent Number: 5,334,537
[45] Date of Patent: Aug. 2, 1994

[54] DIRECT IMMUNOASSAY USING PH-SENSITIVE FLUOROCHROMES

[75] Inventors: Cheng S. Lee, Columbia; Ping Y. Huang, Baltimore, both of Md.

[73] Assignee: The University of Maryland, College Park, Md.

[21] Appl. No.: 791,309

[22] Filed: Nov. 14, 1991

[51] Int. Cl.$^5$ .................. G01N 33/543; G01N 33/536
[52] U.S. Cl. ..................... 436/518; 436/536; 436/546; 436/800
[58] Field of Search ............... 436/518, 536, 546, 800

[56] References Cited

U.S. PATENT DOCUMENTS

| | | |
|---|---|---|
| 3,998,943 | 12/1976 | Ullman ........................ 424/12 |
| 4,207,075 | 6/1980 | Liburdy ........................ 23/230 |

OTHER PUBLICATIONS

Lee et al. Anal Chem 1991 63 pp. 464–467.
Bright et al. Anal Chem 1990 62 1065–1069.
Friedrich et al. Eur. J. Biochem. 173 pp. 227–231 (1988).
Timasheff et al. in *Protein Structure* Creighton, T. E. ed, IRL Press (1989) p. 337.
Zubay, Geoffrey *Biochemistry* (1983) Addison-Wesley Publishing Company, Inc. p. 51.
Ullman et al. JBC 251 #14 pp. 4172–4176 (1976).
Nargessi: et al. Methods of Enzymology 74 pp. 60–79 (1981).
Smith FEBS Letters 77 #1 pp. 25–27 (1977).
Meadows et al. J. Immunol. Meth. 143 pp. 263–272 (1991).

*Primary Examiner*—Esther L. Kepplinger
*Assistant Examiner*—Lora Marie Green
*Attorney, Agent, or Firm*—Oblon, Spivak, McClelland, Maier & Neustadt

[57] ABSTRACT

The complexing of an antibody-antigen binding pair is determined by observing the change in fluorescence of a pH-sensitive fluorochrome attached to one of the members of the binding pair. When the binding is conducted in a solution having a pH other than the isoelectric point of the antibody, there will be a change in the pH of the microenviromnent surrounding the fluorochrome. This change will correspond to a change in the observed fluorescent intensity. Either member of the binding pair can be labeled, and combined with that member whose presence is suspect, in an immunoassay.

7 Claims, 5 Drawing Sheets

FIG. 3B  $\% = \dfrac{I_{PA-FLUORESCEIN\ \&\ IgG} - I_{PA-FLUORESCEIN}}{I_{PA-FLUORESCEIN}}$ FIG. 4B  $\% = \dfrac{I_{PA-FLUORESCEIN \& IgG} - I_{PA-FLUORESCEIN}}{I_{PA-FLUORESCEIN}}$

DIRECT IMMUNOASSAY USING PH-SENSITIVE FLUOROCHROMES

Field of the Invention

This invention pertains to a direct, homogeneous immunoassay, for the detection of an antibody-antigen specific binding event. More precisely, the invention comprises the detection of antibody-antigen binding by reliance on changes in fluorescence of pH-sensitive fluorochromes complexed with either member of the antibody-antigen complex, induced by changes in the microenvironment relative to the fhorochrome due to formation of the antibody-antigen complex.

BACKGROUND OF THE PRIOR ART

The identification, analysis and monitoring of biological compounds, most importantly proteins, polysaccharides and the like, has become increasingly important for research and industrial applications, as well as health care fields, demographic analysis and the like. Conventionally, biological analyte detection systems are based on detection of an antibody binding to the suspected antigen in the analyte, or vice-versa, and somehow determining the (1) event of binding and (2) Mount of binding between antigen and antibody occurring. In general, the specific binding pair (wherein the antibody is specific for the antigen, and will not bind to non-antigen mimics) is referred to as an antibody-antigen complex, or immunocomplex. If the occurrence of binding per se, is all that is measured, the assay is qualitative in nature. Increasingly, however, quantitative measuring, i.e., the amount of binding, is of concern. Such quantitative analysis requires enhanced sensitivity as well specificity.

One dominant form of immunoassay providing information of this type is the sandwich ELISA, wherein an antibody, bound to a stable support surface, is admixed with the analyte, and antigen present in the analyte is bound to the previously bound antibody. The surface binding the antibody is then washed to remove debris. Thereafter, the bound antigen is contacted with a preparation of another antibody, this second antibody bearing a reporter molecule or label of some sort which can be detected. The second antibody will bind to the exposed and bound antigen, and after a second washing, the Mount of second antibody bound can be detected, by determining the label concentration. The sandwich assays can be competitive or non-competitive in form. They require, however, at a minimum, the preparation of two different antibodies, several wash steps, and introduce a series of reactions which must be detected, and thus, the reliability and sensitivity of the assay is dependent upon repeated complexing events.

In response to these difficulties, a variety of more direct assays to detect the formation of the immunocomplex have been developed. Thus, a variety of assays have been developed to measure the specific binding of an antigen-antibody specific binding pair, by attaching a fluorescent label, such as fhorescence to one element of the binding pair, and attaching a quenching particle, that is, a molecule or molecular fragment which quenches the fhorescent activity of the fhorescent label, to the other binding pair. The fluorescence of the fluorescent-label-bound element is monitored as it is added to the second element. The binding of the antibody and the antigen brings the quenching moiety in close proximity to the fluorescent label, extinguishing or reducing the degree of fluorescence. Thus, a reduction in detected fhorescence is indicative of binding, and the degree of reduction is indicative of the degree or amount of binding. U.S. Pat. Nos. 3,996,345, Ullman et al, 4,650,770, LiU et al, 4,351,760, Khanna, 3,998,943, Ullman and 4,806,488, Berger et al, all describe variations on this theme. In an alternative, but related format, one of the antibody or antigen ligand is labeled with a reporter molecule, and the complexing of the antibody and antigen inhibits the attack on the label, by some subsequently added agent. Thus, U.S. Pat. No. 4,208,479, Zuk et al, adds a modifying agent after formation of the immunocomplex, which modifying agent may be light. Unbound label will be altered by the modifying agent, to fluoresce at a different wave length, or give off a different degree of fluorescence, allowing distinction between bound and unbound label. Similarly, U.S. Pat. No. 4,816,419, Halfman, calls for the addition of a surfactant to a immunocomplex-containing preparation. Either the antigen or the antibody of the complex is labeled with a fluorescent dye. The surfactant forms micelles awhich sequester unbound label material, thereby quenching the label, while bound label will continue to fluoresce. In a third alternative, various dye sequences, or selective dyes, are used, the spectral absorbance of the dye shifting upon formation of the immunocomplex. Assays of this type are addressed in U.S. Pat. No. 4,568,647, Sanford, and U.S. Pat. No. 4,166,105, Hirschfeld.

All of the above direct assays are characterized by the need to interact the fluorescent label with a second molecule or moiety of some type, which alters the degree of fhorescence. This requires additional complexing, which may be difficult when the antigen is not readily identifiable. Further, most of these sequences require additional washes, where an agent is added to the complex, to alter the characteristics of the fluorescence.

Accordingly, it remains a goal of those of ordinary skill in the art to provide a direct, homogeneous assay for antigen-antibody specific binding, which allows both qualitative and quantitative determination of the presence of the antigen-antibody complex.

SUMMARY OF THE INVENTION

The above goal, and more specific goals discussed in detail below, are met by an assay based on changes in the microenvironment of a fluorescent label on either the antigen or antibody to be bound. In such assays, one begins either with the antigen or antibody of the sought binding pair. The presence, or likelihood, of certain specific pathological conditions can be determined by the presence of an antibody in an individual's body fluids. In these cases, one begins with the antigen, labeling the antigen, and admixing it with the analyte suspected of containing the antibody. In other circumstances, an antibody specific for a suspected antigen, frequently a pathogen, is raised and harvested from a cell line or other source. This antibody is labeled with a fluorescent label, and then introduced to the analyte. In either event, when the immunocomplex of antigen and antibody is formed, the microenvironment of the reporter label, the fhorescent label, is altered. In particular, the distribution of electrical charges, or the electrostatic environment, of the immunocomplex, is altered, provided the pH is other than the isoelectric point of the antibody involved. At pH values below the isoelectric point, the antibody carries a net positive charge. (At pH values above the isoelectric point, the reverse distribution occurs). When complexing with the antigen, the positive electric field around the complex is increased. This increase in the positive electric field will attract counter ions from the surrounding solution, generally OH-, in the case of conventional buffers. This results in an increase in the local pH relative to the label, although the pH of the entire solution remains constant. The change in the local environment of the label will alter its fluorescing characteristics, such that difference in fluorescence intensity in complexed and non-complexed label-bearing material can be easily detected. A shift in fhorescence is a qualitative indication of immunocomplexing. The degree or Mount of shift in fluorescence detected is a quantitative indication of the degree of complexing.

DETAILED DESCRIPTION OF THE INVENTION

This invention employs, as reporting molecules, fhorescent labels. In particular, the fluorescent label should be pH sensitive. There are a wide variety of pH-sensitive fhorochromes, of which fluorescein is perhaps most prototypical. Other pH-sensitive fhorochromes may be used as well, and those of ordinary skill in the art will quickly recognize a wide variety of pH-sensitive reporter labels. Among these, those of skill in the art will recognize umbelliferones (coumarin compounds), pyrenes, resorufin and generally, hydroxy esters of aromatic acids. Other pH-sensitive fhorochromes will occur to those of skill in the art, and are generally suitable for use with the claimed invention. In addition, electrostatic potential sensitive fhorochromes such as styryl dyes and tetramethyl rhodemine dyes are also suitable for use with the claimed invention.

In general, in the inventive immunoassay, one will have the identity of either the antibody or the antigen, and be searching for the presence of the other. Either ligand binding member can be labeled with the pH-sensitive fluorochrome, which shall be referred to, for convenience here, as fluorescein. Thus, if an analyte is to be sampled for the presence of an antigen, the captive antibody can be labeled with the fluorescein. In the alternative, if the antigen is known, and one is searching for the presence of the antibody, the antigen, generally a protein or a polysaccharide, can be labeled. It should be specifically noted that while it is convenient, it is not necessary, in this immunoassay, to attach the labeled binding pair member to a solid support. The assay may be an entirely single phase assay.

Figure 1:
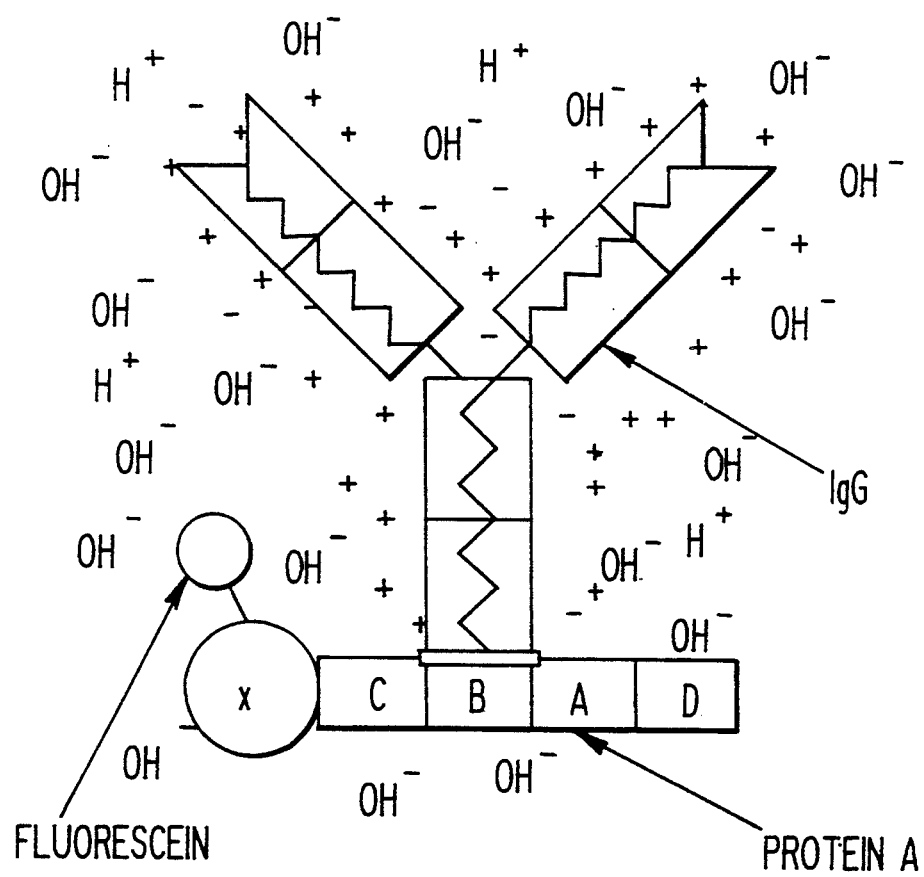
FIG. 1 is a schematic representation of the microenvironment observed by a fluorescent reporter label upon the complexing of an antibody (mouse IgG) and an antigen (protein A).
Figure 2:
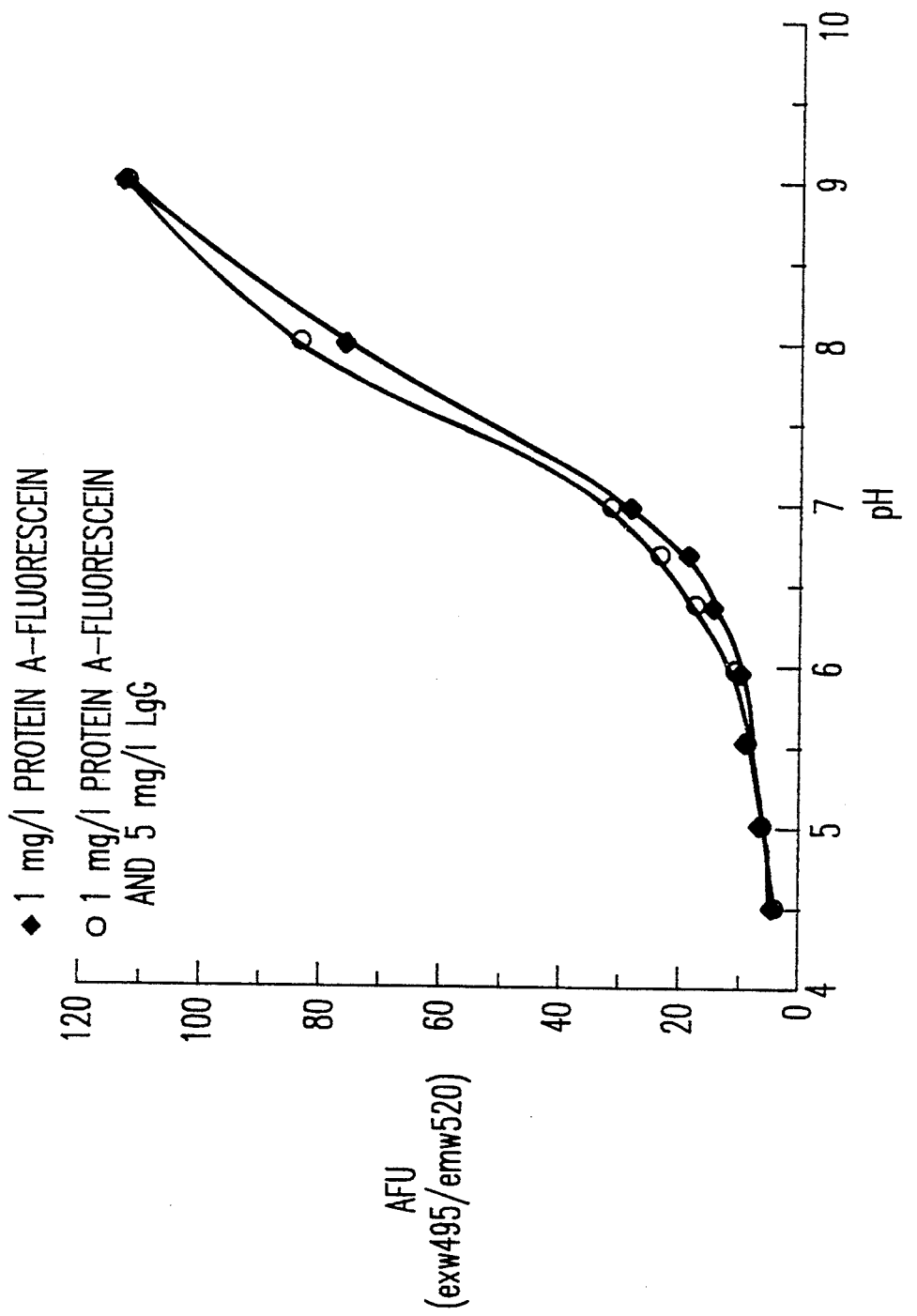
FIG. 2 graphically compares the fluorescent intensity observed in non-complexed protein A provided with a fluorescent label and that observed when the labeled protein A is complexed with mouse IgG. The shift is observed as a function of pH.

The invention is premised on the observation that the antibody carries a net positive charge in solution, when the solution has a pH below the isoelectric point (PI) of the antibody. Similarly, the protein antigen will reflect a significant positive charge. When these two complexing members are in fact Joined to form the immunocomplex, the positive charged antibody contributes to an increased positive electric field around the immunocomplex. This results in a migration of counter anions to the area immediately adjacent the fluorochrome (the microenvironment). This effect is clearly illustrated in FIG. 1. As a result, the pH in the microenvironment is altered, although the pH of the solution itself, in bulk, remains constant. This induces a change in fluorescent intensity, that is, there is a difference in observed fluorescent intensity when the binding pair member that is labeled is free, and when it is complexed with the remaining binding pair member. This is clearly illustrated in FIG. 2, wherein protein A is labeled with fluorescein, and complexed with mouse IgG. These are the same ligand binding pairs addressed throughout the figures. Other antigen-antibody systems such as protein A-Human IgG- Anti IgG vital surface antigens - antibodies are also suitable for use with the claimed invention, provided the local electrostatic enviromment is changed upon the antigen-antibody binding.

Figure 3A:
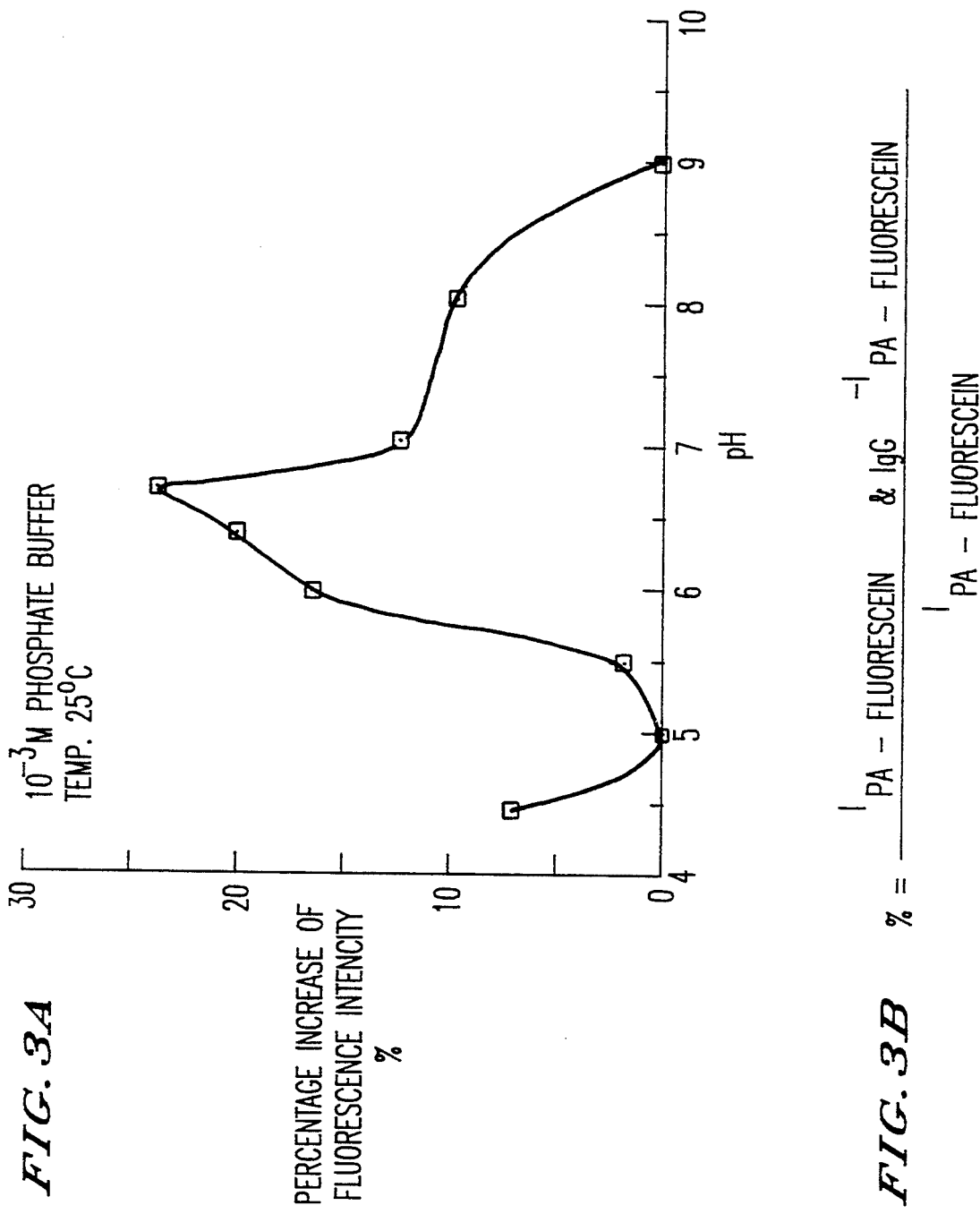
FIG. 3 observes the degree of change (increase) of fhorescent intensity after complexing as a function of pH of the overall solution.

The change in fluorescence or fluorescent intensity, is a function of a variety of factors, including the pH of the bulk solution, the buffer concentration, and the like. The influence of both pH and buffer concentration (ionic strength) is reflected in FIGS. 3 and 4, respectively.

Thus, the farther away from the PI of the antibody, the greater the change in fluorescent intensity after complexing. It should be noted that even close to the PI, substantial changes are observed on a repeatable basis, such that the complexing event can be detected.

Figure 4A:
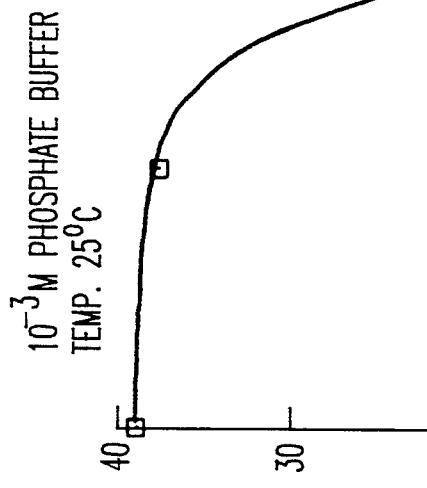
FIG. 4 graphically illustrates the degree of change of fhorescence after binding as a function of buffer concentration.
Figure 5:
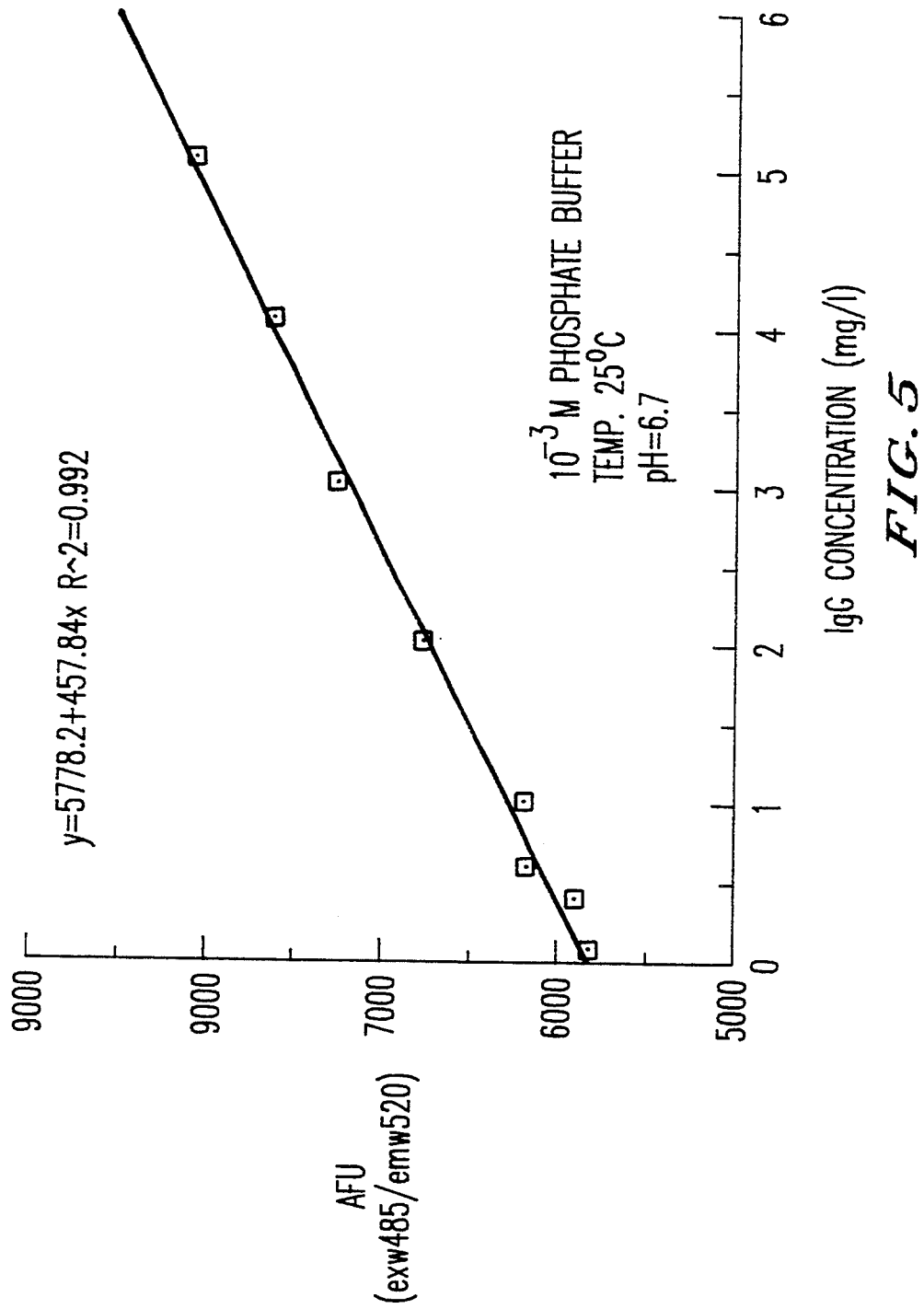
FIG. 5 is a calibration curve, comparing fhorescent intensity versus antibody concentration given a constant labeled antigen concentration.

Similarly, buffer concentration will effect the degree of change observed, as reflected in FIG. 4. As a general rule, the lowest permissible buffer concentration that maintains the bulk solution pH is preferable for use in the invention.

The above-discussed results were obtained by conjugating protein A with fluorescein (5 fluorescein molecules per protein A molecule). Methods of conjugation are well known in the art, and do not constitute an aspect of the invention, per se. The conjugated protein A was obtained from Molecular Probes of Oregon. As noted above, either the antigen or the antibody can be conjugated with the reporter label. A common conjugation agent is fluorescein isothiocyanate for antibodies such as mouse IgG. In the experiments discussed above, the protein A fluorescein conjugate (1 microgram/ml) was introduced to a solution of a 1 mM potassium phosphate buffer, pH 6.7. This solution was equilibrated, and the fluorescence emission spectra was obtained. Mouse IgG was introduced to the solution, and maintained at 25° C. for a fifteen minute incubation period. The PI of mouse IgG is 9.5. Although there was no shift in maximum emission wavelength, a change in fluorescent intensity was observed, to the phenomenon explained above with regard to FIG. 1, i.e., a more alkaline microenvironment surrounding the label.

The effect of pH on intensity was measured with regard to the same incubation solution discussed above (2 micrograms/ml IgG), while altering the pH. Fluorescence intensity both before and after immunocomplexing reached a maximum at a pH of about 5.5.

Similarly, the effect of buffer strength was measured on the same binding solution, with the results reflected in FIG. 4. At higher ionic strength, there are more counter ions available to balance the electrostatic potential. Thus, the effectiveness of the conjugated fluorescein for sensing the changes in local electrostatic environment upon immunocomplexing decreases upon an increase in buffer strength.

Accordingly, the invention that is the subject of this application is applicable wherever the ligand binding pair cause, upon immunocomplexing, a change in the microenvironment of the label, which in turn depends upon the electrostatic potential of that microenvironment. When the pH of the macroenvironment is other than the isoelectric point of the antibody, the observed phenomenon will occur. The invention accordingly is not to be limited by the above examples, save for the limitations in the claims below. In particular, specific antibodies, antigens, fluorochromes and the like can be selected without departing from the scope of the invention, save for the limitations recited in the claims.

What is claimed is:

1. A method of directly detecting complexing of an antigen/antibody binding pair, comprising:
   a) preparing a solution of one of said members of said binding pair complexed with a fluorochrome selected from the group consisting of fluorescein, umbelliferones, pyrenes, resorfins, hydroxyesters of aromatic acids, styryl dyes and tetramethyl rhodamine dyes said fluorochrome being complexed with said one of said members of said binding pair at a point spatially proximal to a binding site for said antigen/antibody binding pair in a buffer having a pH other than the isoelectric point of said antibody, and determining the intensity of fluorescence thereof,
   b) adding said remaining member of said binding pair to said solution and monitoring the intensity of the fluorescence of said solution,
   c) wherein a change in fluorescent intensity in said solution after step b corresponds to the complexing of said antigen with said antibody said solution being free of molecular moieties which affect the intensity of the fluorescence of said fluorochrome, said change in fluorescent intensity being induced by a change in the microenvironment of said fluorochrome induced by said complexing event.

2. The method of claim 1, wherein said member of said binding pair complexed with said fluorochrome is said antigen.

3. The method of claim 1, wherein said binding pair member complexed with said fluorochrome is said antibody.

4. The method of claim 1, wherein said fluorochrome is fluorescein.

5. The method of claim 1, wherein said binding pair member not complexed with said fluorochrome is contained in an analyte.

6. The method of claim 1, wherein said fluorochrome is a pH-sensitive fluorochrome.

7. The method of claim 1, wherein said fluorochrome is an electrostatic potential-sensitive fluorochrome.

* * * * *